United States Patent [19]
Gao et al.

[11] Patent Number: 5,804,145
[45] Date of Patent: Sep. 8, 1998

[54] APPARATUS FOR THE PREPARATION OF MICROSCOPE SLIDES

[75] Inventors: Daniel Dashui Gao, Miami; Cynthia J. Sperber, Fort Lauderdale, both of Fla.

[73] Assignee: Coulter International Corp., Miami, Fla.

[21] Appl. No.: 821,839

[22] Filed: Mar. 21, 1997

Related U.S. Application Data

[62] Division of Ser. No. 555,688, Nov. 14, 1995, Pat. No. 5,650,332.

[51] Int. Cl.⁶ .................................................. G01N 33/49
[52] U.S. Cl. ........................... 422/101; 436/174; 427/2.11
[58] Field of Search ............................ 422/101; 436/174; 427/2.11, 2.13

[56] References Cited

U.S. PATENT DOCUMENTS

| | | | |
|---|---|---|---|
| 3,495,926 | 2/1970 | Naz | 422/101 |
| 3,995,022 | 11/1976 | Heanley et al. | 424/3 |
| 4,061,108 | 12/1977 | Levine et al. | 118/100 |
| 4,378,333 | 3/1983 | Laipply | 422/100 |

*Primary Examiner*—Lyle A. Alexander
*Attorney, Agent, or Firm*—Warren W. Kurz

[57] ABSTRACT

An improved method and apparatus for making blood smears on microscope slides are disclosed. The method is characterized by the step of temporarily deforming the normally planar surface of a slide on which the smear is being made, rendering it slightly concave in shape. This step has been found to substantially reduce streaking and other artifacts which interfere with the formation of an uninterrupted, substantially uniform monolayer of blood cells on the slide. Preferably, the movement of a blood-smearing member across the slide is controlled as a function of various predetermined physical parameters of the blood.

3 Claims, 9 Drawing Sheets

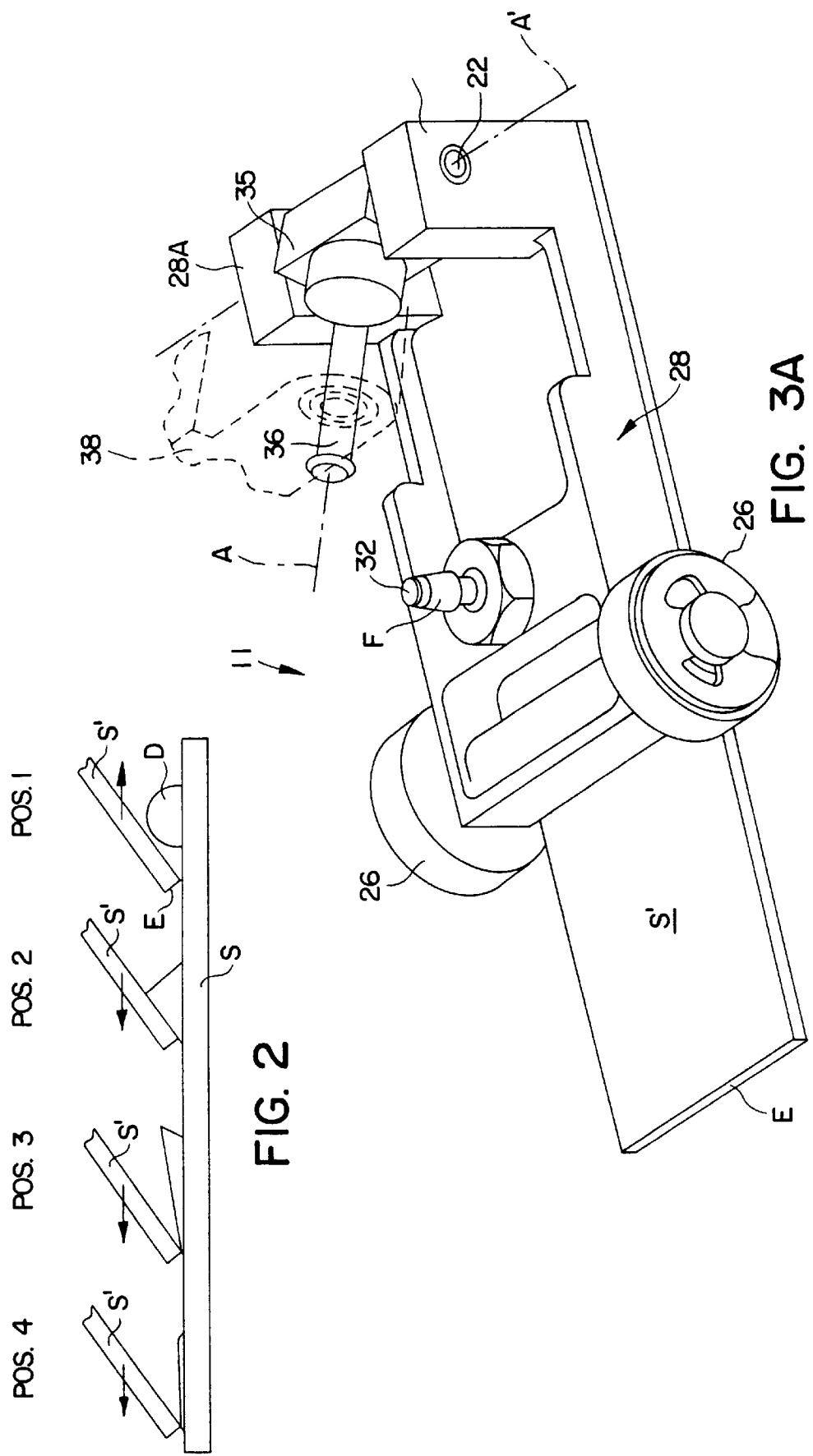

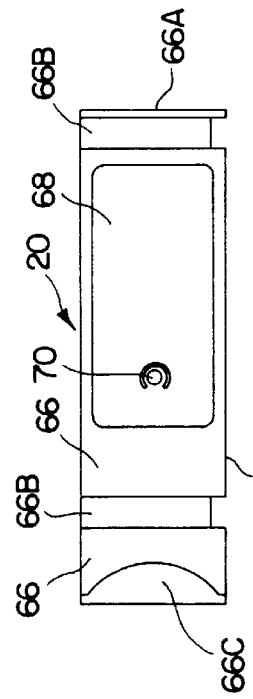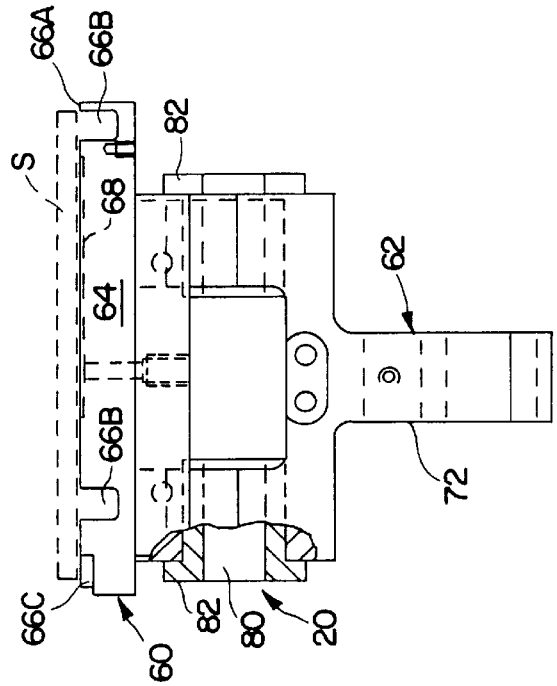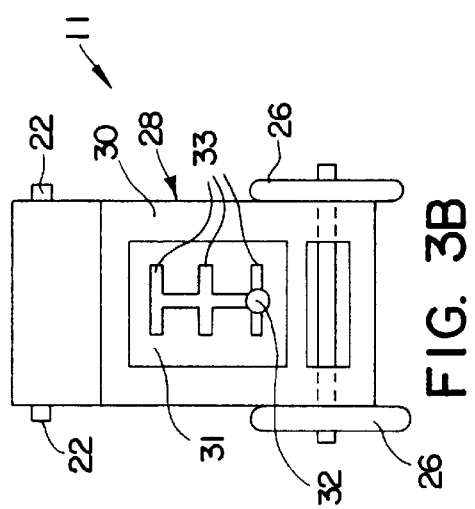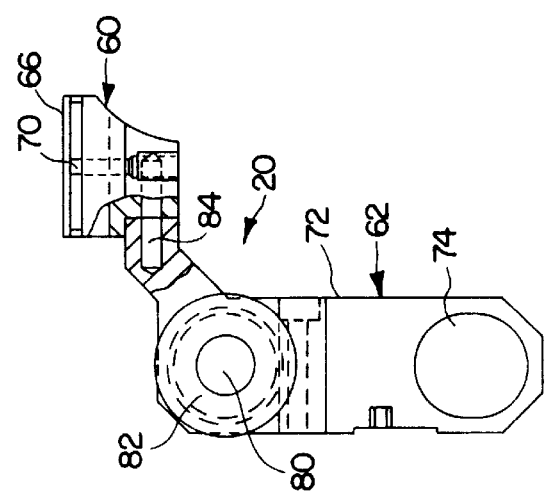

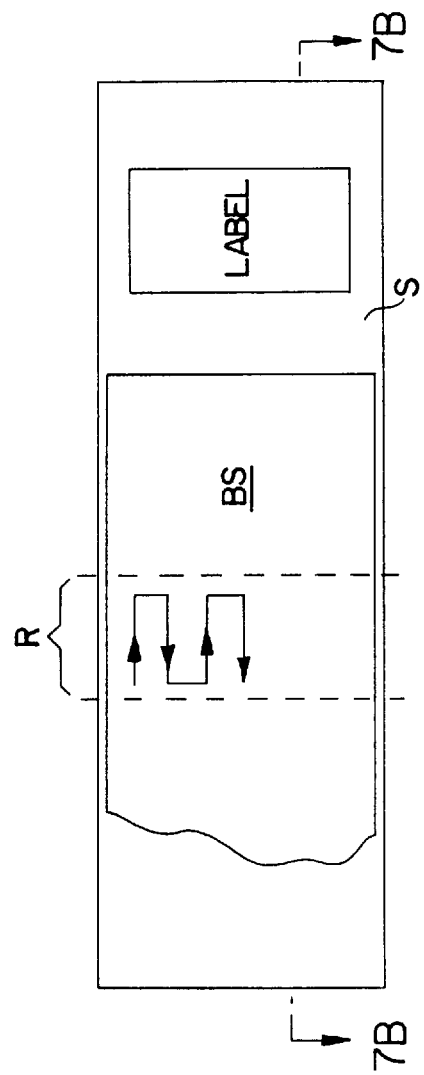
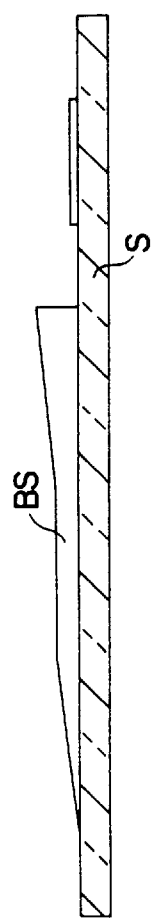

APPARATUS FOR THE PREPARATION OF MICROSCOPE SLIDES

This is a Divisional of application Ser. No. 08/555,688 filed Nov. 14, 1995 now U.S. Pat. No. 5,650,332.

CROSS REFERENCE TO RELATED APPLICATIONS

Reference is made to the following commonly assigned, concurrently filed U.S. patent applications, the contents of which being incorporated herein by reference: (1) U.S. application Ser. No. 08/557,226, entitled "Improved Apparatus and Method for Automated Production of Blood Smear Slides" now abandoned; (2) U.S. application Ser. No. 08/557,229, entitled "Blood Analysis System Having Blood Storage, Transport and Automatic Slide-Making Capabilities" now U.S. Pat. No. 5,665,312; (3) U.S. application Ser. No. 08/557,228, entitled "Improved Method and Apparatus for Drying Blood Smear Slides" now U.S. Pat. No. 5,766,549; (4) U.S. application Ser. No. 08/555,687, entitled "Pinch Pump for Dispensing Fluid from a Flexible Fluid Conduit" now U.S. Pat. No. 5,674,052; and (5) U.S. application Ser. No. 08/557,230, entitled "Cassette for Blood Smear Slides and Cooperative Slide Ejection Assembly".

BACKGROUND OF THE INVENTION

1. Field of the Invention

The present invention relates to improvements in methods and apparatus for automatically spreading or "smearing" a fluid specimen on a microscope slide for subsequent analysis. The invention is particularly useful for producing a blood smear on a microscope slide for blood cell analysis.

2. Discussion of the Prior Art

Microscopic examination of biological fluids (e.g. blood, urine, etc.) on glass slides is an old and well-known technique used for diagnosing and evaluating a patient's health. Examination of a smeared sample of fluid on a glass slide often permits a physician or clinician to more accurately analyze a fluid sample and to diagnose a variety of fluid-related disorders.

To conduct such observational analysis of fluid samples, it is highly desirable that the slide be prepared in such a manner that a substantially uniform "monolayer" of fluid cells is formed on at least a portion of one of the slide's planar surfaces. A monolayer assures that individual cells can be examined without being masked by overlying cells. Having produced the desired monolayer, the examining clinician or researcher can count the number of cells of different types and/or examine the cell morphology.

Presently, the most commonly used method of producing an examinable blood ssmear on a glass microscope slide is a manual method in which two slides are used. Normally, such slides are approximately 3 inches (75 mm) in length, 1 inch (25 mm) in width and 0.04 inches (1 mm) in thickness. According to the such method, the technician first deposits a drop of blood on the planar surface of one slide and then uses an edge (usually the shorter edge) of the second slide to smear the blood drop on the drop-supporting surface of the first slide. Smearing of the drop is effected by positioning the smearing slide at an acute angle relative to the drop-supporting slide, sliding the smearing slide in a first direction so that the underlying planar surface of the smearing slide contacts the blood drop and allows the drop to wick, due to capillary action, across the width of the smearing slide, and then sliding the smearing slide In the opposite direction, thereby pulling a blood film across the drop-supporting slide by capillary forces. A stain may then be applied to the blood film (usually referred to as a "smear") in order to facilitate the differentiation of the various types of cells.

A problem with the manual technique for producing microscopic slides of blood smears is that there is often a lack of uniformity in the appearance of the smears. This is true even when the same clinician or researcher has prepared all the smears being examined at a given time. As may be appreciated, there are many variables in making a blood smear on a glass slide, including, for example, the volume of the blood drop being smeared, the angle of the smearing member relative to the drop-supporting surface, the rate at which the smearing member moves across the drop-supporting slide, the pressure between the smearing member and the slide, etc. This is further complicated by the fact that the ability to prepare good quality slides varies with the cellular make-up of the blood sample, the surface characteristics of the slide, the edge characteristics of the smearing member and the skill of the slide preparer. In view of these multiple variables, a substantial fraction of blood slides made manually are of little or no use. Unacceptable blood smears include those exhibiting (a) a skewed distribution of cells across the width of the slide, as produced, e.g., by a non-uniform pressure being applied to the smearing edge, and (b) multiple parallel streaks in the blood smear, as produced, e.g., by edge irregularities in the smearing edge of the smearing slide, and (c) smear thickness variations measured in the direction of the smear, as produced, e.g., by irregularities in the frictional characteristics of the drop-supporting planar surface of the slide receiving the smear.

One solution to some of the above-noted problems associated with the manual production of blood smear slides is to provide a device which automates the steps of the manual process. One such device is disclosed, for example, in U.S. Pat. No. 5,209,903, issued in the name of Kanamori, et al. This patent discloses a blood analyzing system which incorporates a conveyor for handling and transporting vials of blood through a blood analyzer and, subsequently, through an automatic blood smear generator. The latter operates to automatically aspirate a blood sample from a vial, deposit a drop of blood on a slide, spread the blood drop to produce a blood smear on the slide, dry the blood smear, print patient information on the slide, and then deposit the slide in a basket adapted for use in a staining bath. Spreading of the blood drop on the slide is effected by the edge of a smearing glass which is used repeatedly to produce multiple slides. Between the making of successive slides, the smearing glass is cleansed by a suitable washing device. While the blood smear is made, the smear-receiving glass slide is maintained in a horizontal position atop a pair of conveyor belts. The rate of movement of the smearing glass, the volume of the blood drop, and the angle of the smearing glass relative to the horizontally oriented drop-supported slide are all variable and operate under the control of a suitable controller which responds to the output of the blood analyzer(s) located upstream of the slide maker along the conveyor belt.

While the automatic slide-making device disclosed in the above-mentioned patent eliminates some of the variables associated with the manual approach to slide making, such device can be problematic in several respects. For example, since the glass smearing member is used repeatedly to make successive slides, apparatus must be provided for cleaning the smearing member between successive slides. Further, since the same smearing member is used to make a large number of slides, any irregularities in the smearing edge of such member can result in streaks which will be exhibited in all slides made by such member. Moreover, since no special care is taken to compensate for any surface irregularities in the smear-receiving glass, variations in thickness of the smear can arise.

SUMMARY OF THE INVENTION

In view of the foregoing discussion, an object of this invention is to provide an improved apparatus and method for producing smears of biological fluid (e.g. blood) on a microscope slide.

In accordance with one aspect of the invention, a method for making a biological fluid smear on a microscope slide includes the steps of: (a) depositing a drop of biological fluid (preferably of about 4 microliters in volume) on a planar surface of a glass slide; (b) temporarily deforming the slide to render the drop-supporting surface thereof concave in shape; and (c) spreading the drop across the drop-supporting surface while such surface is deformed. Preferably, the drop-spreading step comprises the steps of contacting the drop with an edge of a smearing member (preferably a second glass slide) at a location closest to the direction in which the drop is to be spread; moving the smearing member in a direction toward the drop to wick a portion of the drop across the entire smearing edge of the smearing member; and moving the smearing member in an opposite direction, away from the drop, thereby spreading the drop over the concave supporting surface as a result of capillary action between the smearing member and the drop. Preferably, the rate at which the smearing member is moved relative to the drop in order to produce the smear is controlled, both in acceleration and velocity, as a function of the viscosity of the biological fluid. Typically, the higher the viscosity of the fluid, the lower the acceleration and velocity of the smearing member, and vice-versa. When the biological fluid is blood, movement of the smearing member is controlled as a function of various physical properties of the blood sample, especially the hematocrit value. In addition to the hematocrit value of the blood, other parameters of the blood are employed to determine the appropriate acceleration and velocity of the blood-smearing member. Also important in determining the quality of the blood smear is the time period during which the smearing member contacts the blood drop prior to being moved in a direction to produce the blood smear.

According to another aspect of the invention, an apparatus for carrying out the method of the invention is provided. Preferred apparatus generally includes: (a) means for depositing a drop of blood of predetermined volume on the planar surface of a glass slide; (b) means for selectively deforming the slide to render the drop-supporting surface of the slide concave in shape; (c) a smearing member having a rectilinear edge; (d) means for manipulating the smearing member to position the rectilinear edge thereof in contact with the drop-supporting surface of the glass slide; and (e) means for producing relative motion between the smearing member and the glass slide to effect smearing of the blood drop on the concave, drop-supporting surface of the slide. Preferably, such apparatus further includes means for varying the speed and acceleration of the smearing member as a function of the properties of the fluid sample.

As a result of the improved method and apparatus of the invention, substantially more uniform blood smears are made, with little or no evidence of streaking or other artifacts which would render difficult an examination of the smear.

The invention and its various advantages will be better understood from the ensuing detailed description of preferred embodiments, reference being made to the accompanying drawings in which like reference characters denote like parts.

BRIEF DESCRIPTION OF THE DRAWINGS

FIG. 2 is an enlarged partial view of the FIG. 1 apparatus illustrating four positions of the drop-smearing member used to smear a drop of blood on a glass slide;

FIGS. 3A and 3B are top perspective and bottom views of a device used to grasp and manipulate the drop-smearing member;

FIGS. 4A, 4B and 4C are top, end and side views, respectively, of a slide-carrying shuttle having a vacuum-generating section for purposes of deforming a slide carried thereby;

FIGS. 7A and 7B are top and side illustrations of a blood smear slide produced by the FIG. 1 apparatus;

DETAILED DESCRIPTION OF PREFERRED EMBODIMENTS

Figure 1:
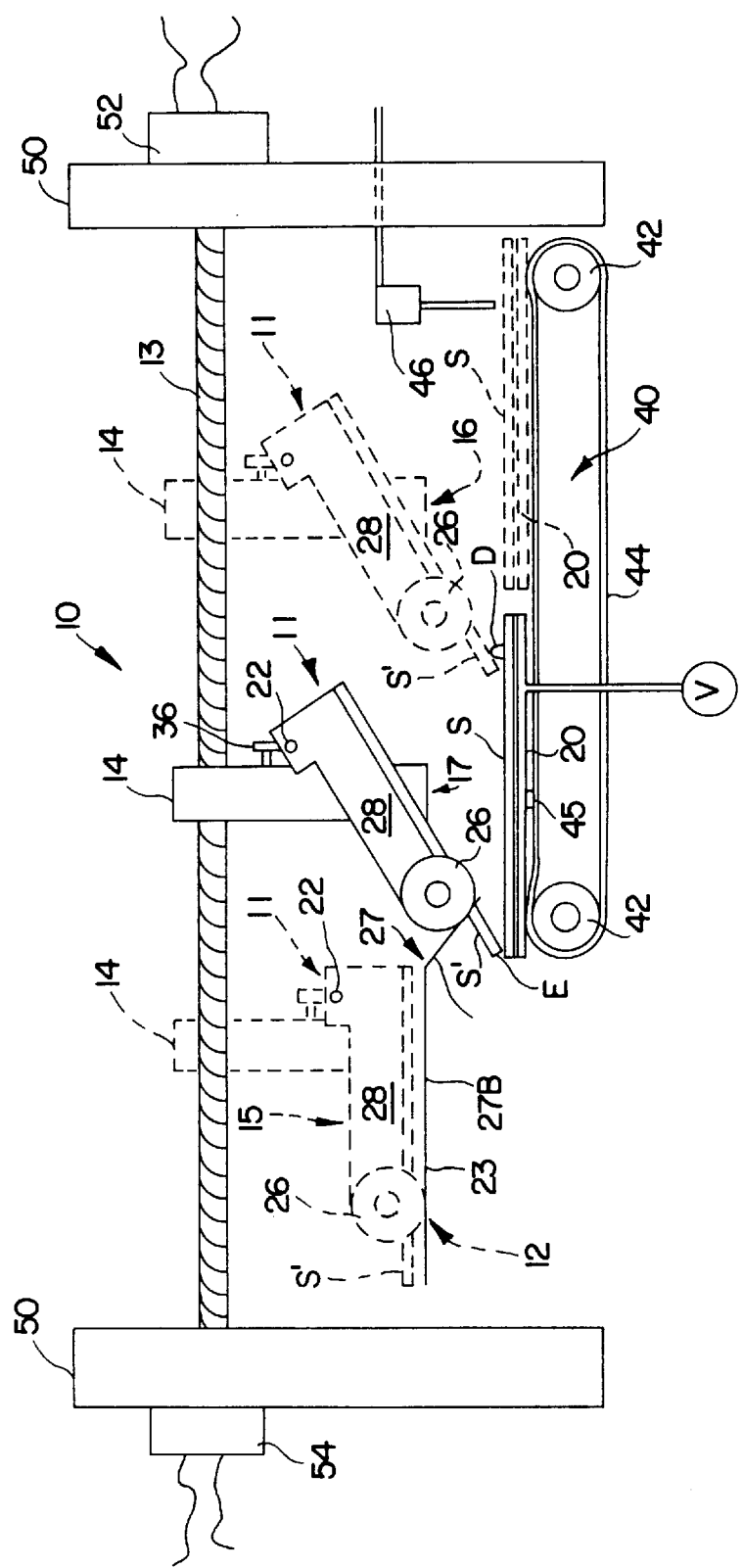
FIG. 1 is a schematic diagram illustrating a side view of a slide-making system embodying the present invention.

Referring now to the drawings, FIG. 1 schematically illustrates a slide making apparatus 10 for producing a blood smear on a conventional glass microscope slide S. Such apparatus operates on the "slide-on-slide" principle disclosed in the aforementioned U.S. Ser. No. 08/557,226 filed concurrently herewith now abandoned and entitled "Improved Apparatus and Method for Automated Production of Blood Smear Slides". According to this principle, one edge of a slide is used to spread a drop of blood on the planar surface of a second slide in order to form a blood smear thereon. After forming the blood smear, the blood-smearing slide is then used as the smear-receiving slide on which a subsequent blood smear is made. Because the blood smear formed on the blood-smearing slide is sufficiently spaced from that edge used to produce the blood smear on the preceding slide, there is no possibility of cross-contamination between successive blood samples and, hence, there is no need to clean the blood-smearing edge of a slide prior to receiving a drop of blood used to make a subsequent blood smear. For a better and more detailed description of the slide-on-slide principle and for a preferred apparatus for carrying it out, the reader is referred to the above-noted application, the disclosure of which being incorporated herein by reference.

As noted earlier, the glass microscope slides used to both receive a blood smear and to spread a blood drop to produce such smear are nominally about three inches in length, one inch in width and about 0.04 inches (1 millimeter) in thickness. It is the shorter edge (i.e. the 1 inch edge) of the blood-smearing slide that is used to spread the blood along the length of the smear-receiving slide. Often, the edges of such slides, as received from most manufacturers, are not finely ground to provide a rectilinear edge; rather, when examined closely, such edges are seen to be relatively "ragged" in shape, having a series of randomly spaced bumps or sharp teeth of different heights protruding from the edge. Obviously, when such an edge is used as a smearing edge to produce a blood smear, the resulting smear can be characterized by a plurality of parallel streaks running in the direction of the smearing movement. Sometimes a clinician will minimize such streaking by selecting a slide having a relatively smooth edge and use that edge to make a series of blood smears, being sure to dean the smearing edge between making successive blood smears. But in using the above-described slide-on-slide approach to making blood smears, it will be appreciated that each blood smear is made by the edge of a different slide; hence, the streaking artifact can often appear in the resulting blood smears. The elimination of such artifacts represents a major technical problem addressed by the present invention.

In addition to exhibiting ragged edges, conventional microscope slides can also exhibit surface irregularities which tend to randomly impede or accelerate the movement of a blood-smearing member moving across the slide surface. The result, as indicated above, is a "stuttering" movement of the smearing member which gives rise to thickness variations in the smear, as measured in the direction of the smear. The elimination or reduction of this artifact is another technical problem addressed by the present invention.

The slide-making apparatus of FIG. 1 comprises a slide-manipulating device 11, sometimes referred to as a "slide truck", which is mounted for movement along a lead screw 13 via a coupling member 14. As the lead screws turns in one direction, the slide truck moves from a position 15, at which the slide truck picks up a glass slide S' from a slide-supply station 12, toward a position 16, at which the slide's edge E is positioned to contact a drop of blood D on the planar surface of glass slide S. As the lead screw rotates in the opposite direction, the slide truck begins its blood-smearing travel toward an intermediate position 17 at which the blood smearing slide S' has completed its blood-smearing travel and is positioned to be dropped onto a movable shuttle 20, such as by the release of a vacuum force used to hold the slide on truck. Since shuttle 20 supports the glass slide S at the time a drop is spread thereon, a slide-ejection mechanism (not shown) is provided to remove slide S from the shuttle prior to the deposit of slide S' thereon.

The blood-smearing movement of smearing slide S' over the planar surface of slide S is illustrated in FIG. 2. In Position 1, the slide truck has positioned slide S' so that its smearing edge E is slightly downstream (relative to the intended smearing direction) of the blood drop D. Lead screw 13 is then rotated to cause the under surface of the smearing slide to move into contact with the drop, thereby allowing the fluid to wick (by capillary action) across the entire width of the smearing slide, in the vicinity of the smearing edge E. This is illustrated in Position 2. Thereafter, the lead screw is rotated in the opposite direction to cause the smearing slide to move through Position 3, in which the thickness of the smear has been reduced to about a monolayer of blood cells, and then to Position 4 in which the monolayer has been spread over a portion of the slide surface. It will be noted that the blood smear has been produced by "pulling" the blood film over the slide surface, rather than by pushing the blood by edge E. This pulling of the film across the slide is the standard and preferred technique in that it minimizes damage to the cells during the smear formation.

As shown in FIG. 1, the slide truck is mounted for pivotal movement about a pair of pivot pins 22 supported (as described below) by coupling member 14. The slide truck includes a pair of wheels 26 which, during a portion of the slide truck travel along the lead screw 13, engage a pair of spaced ramps 27 having an inclined portion 27A and a horizontal portion 27B. As the slide truck wheels move along the ramps, the slide truck pivots from a horizontal orientation (shown in position 15), in which the base of the truck is positioned to grasp a slide from the slide supply station, to an angular orientation (shown in positions 16 and 17) in which the blood-smearing slide S' is angularly disposed with respect to the planar surface of a slide supported by shuttle 20, such angle being fixed at approximately 20° with respect to horizontal. In its angular orientation, the slide truck supports slide S' so that its blood-smearing edge E rests slightly below the plane of the drop-receiving surface of slide S.

The details of the slide truck 12 are better shown in FIGS. 3A and 3B which illustrate that the truck comprises a body portion 28 having a slide-receiving platform 30 as its bottom surface. Platform 30 has recess 31 formed therein, the latter communicating with a vacuum port 32 to which a vacuum source (not shown) is connectable via a suitable fitting F. When a vacuum is applied to port 32 while platform 30 is closely spaced from a slide S at the slide-supply station 12, the slide will be drawn to and held against the platform by the vacuum pressure. A plurality of raised ribs 33 formed in the recess serve to prevent any deformation of the smearing slide S' while it is drawn to and supported by platform 30. Preferably, the slide truck is supported by coupling member 14 for "universal" movement about a pair of mutually perpendicular axis, A, A', whereby the smearing edge E of the supported slide S' will maintain a substantially uniform pressure on the underlying planar surface of the slide receiving the blood smear. Such universal movement is provided by a block 35 which is both rotatably mounted for movement about Axis A on pivot pins supported by a pair of opposing uprights 28A and 28B of housing 28, and rotatably mounted for movement about axis A" on a shaft 36 carried by an arm 38 supported by coupling 14. The weight and center of gravity of the slide truck are selected so as to apply only sufficient weight by the edge of the smearing slide S' to result in a monolayer of blood being spread over the "examination area" (as discussed below) of the blood smear. Typically, the weight of smearing edge is about 13 grams.

Referring again to FIG. 1, slide shuttle 20 is mounted for movement along a rectilinear path by an endless conveyor 40, whereby the shuttle moves between a blood drop-depositing position, shown in phantom lines, and a blood-smearing position, shown in solid lines. The conveyor may comprise a pair of spaced rollers 42 which support a conveyor belt 44 to which the shuttle is connected by a coupling 45. When the slide shuttle 20 is located in the drop depositing position, a blood drop dispenser 46 operates to deposit a metered amount of blood, preferably a drop having a volume of approximately four microliters, onto the surface of a glass slide S. The amount of blood to be delivered onto the slide must be very precisely metered, typically on the order of about 3 µl to 5 µl, preferably 4 µl±1 µl and most preferably 4 µl±0.5 µl. The blood can be delivered to the blood deposition device, although it is not required, for deposition on the slide 20 by means of a pump such as is disclosed in co-pending U.S. application Ser. No. 08/555,687, entitled "Pinch Pump for Dispensing Fluid from a Flexible Fluid Conduit" now U.S. Pat. No. 5,674,052. Upon depositing a drop of blood on slide S, the conveyor is activated to move the shuttle and its supported slide to the slide position shown In solid lines. In this position, the smearing slide S' can then contact the blood drop and, as described above, and produce the desired blood smear. A vacuum source V serves to firmly secure slide S to the shuttle and, as explained below, to deform the slide while the smear is made. After depositing a smearing slide S' onto the shuttle, the slide truck is then moved back up the ramp 27 to pick up a new slide S' which is used as a smearing member for smearing blood across the planar surface of the slide just deposited onto the shuttle. Simultaneous to picking up the new smearing slide S', the previously deposited slide S is moved from the smearing position to the blood deposition position.

With respect to the drive mechanism for drive screw 13, the screw is illustrated as being supported by a pair of columns 50. One of the columns also supports a conventional stepper motor 52 for selectively rotating the lead screw, and the other column supports a shaft encoder 54 or the like for monitoring the rotational position of the lead screw.

Now, in accordance with an important aspect of the invention, it has been found, quite unexpectedly, that the quality of the blood smear on a slide can be significantly enhanced if, during the production of the blood smear, a portion of the normally planar, smear-receiving surface of the slide is deformed so as to render it concave in the vicinity of the blood drop. Preferably such concave deformation is produced both in the direction of the smear, i.e., along the length of the slide, as well as in a direction transverse to the smear, i.e., across the width of the slide. It is also preferred that the point of maximum deformation of the smear-receiving slide be in the vicinity of the deposited blood drop so that, at the beginning of the smear, a small "well" of fluid is formed across the slide from which the smear is taken. While the reasons for the enhanced results are not entirely understood, it has been observed that the aforementioned artifacts, i.e. streaking and smear thickness variations, are dramatically reduced by such deformation. It is suspected that, since the smearing edge of the smearing slide contacts only the lateral regions of the deformed slide during the blood-smearing motion of the smearing slide, the ragged nature of smearing edge has less effect in producing the streaking artifact, i.e., compared to a smearing edge that makes contact over the entire width of a non-deformed, smear-receiving slide. Also suspected is that, as a result of the deformation, some of the blood may wick under the smearing edge by capillary forces, as opposed to shearing forces, and thereby act as a smoothing layer which minimizes variations in the dynamic friction between the smearing edge and the planar surface of the smear-receiving slide. Preferably, the maximum deformation of the smear-receiving slide is between about 0.0005 and 0.001 inch (0.0125 and 0.025 mm). To provide such slide deformation, the slide shuttle 20 is specially designed, as described below.

Referring to FIGS. 4A–4C, a preferred slide shuttle 20 generally comprises a slide-supporting/deforming portion 60, and a guiding portion 62 for guiding the shuttle along a rectilinear path between its drop-smearing and drop-dispensing positions. Portion 60 comprises an elongated body 64 having a planar platform 66 for supporting a slide. Platform 66 is of rectangular shape, similar to that of a slide, and slightly larger than the largest slide to be accommodated thereby. A raised edge 66A is provided for registering one end of a slide S at the "head" of the platform so that the blood smear is always produced on the same portion of each slide. A pair of spaced, parallel grooves 66B are provided in the platform to enable a pair of slide-ejection fingers of a slide-ejection mechanism (not shown) to slip under the slide and remove the slide from the platform after a smear is made. An arcuate notch 66C is provided in the foot of the platform to facilitate the accurate deposit of the smearing slide on the platform after such slide has been used, as described above, to smear a blood drop on a slide positioned on the platform prior to such deposit. Platform 66 further includes a cut-out or recessed region 68 for generating a vacuum underneath a supported slide S. The recessed region has a vacuum port 70 through which a vacuum can be drawn. The positioning of the vacuum port within the recessed region is unimportant. What is important, however, is that (a) the applied vacuum force applied through port 70 is sufficient to draw down and thereby deform that portion of a slide that overlies it, and (b) the depth of the recessed region and the applied vacuum force are sufficient to allow the center of that portion of the slide overlying the recessed region to deflect sufficiently to achieve the desired effect, i.e. enhanced smear quality. Preferably, the geometric center of the recessed portion underlies that portion on the slide that receives the blood drop. As noted above, a sufficient deflection or deformation of the slide portion underlying the blood drop is between 0.0005 and 0.001 inch. A preferred depth for region 68 is about 0.06 inch (0.150 mm. In the case of a standard slide, the recessed or cut-out region 68 measures about 1.6 inches (40 mm) in length, and about 0.6 inches (15 mm) in width. The center of the recessed region, which corresponds to the location of maximum deformation of the slide, lies on a line midway between the lateral edges of shuttle platform and, as already noted, directly beneath that portion of the slide that receives the blood drop. Preferably, the top of the recessed region, i.e., the edge away from the smearing direction, begins at about 0.2 inches ((5 mm) from the top edge of the slide. Thus, beginning from the position on the slide located at about the center of the cut-out region 68, a smear is made which is about 1.5±0.1 inches (37 mm) in length, ending about 0.45 inches (12 mm) from the end edge of the slide. The spacing between the lateral edges of platform 66 and the lateral edges of the recessed region 68 is sufficient to prevent a loss of the requisite vacuum pressure, due to leakage between the opposing surfaces of the slide and platform, during the production of the smear. A suitable spacing is about 0.10 to 0.20 inch (2.5 to 5 mm).

The slide-guiding portion 62 of the shuttle 20 comprises a downwardly extending member 72 which defines an opening 74 having bearing surface adapted to ride on a guide rail (not shown) of the slide-making apparatus. Member 72 also defines a channel 80 of circular cross-section. The latter supports a pair of sleeve bearings adapted to surround a rod 80 which extends parallel to rail 78. The shuttle is moved along the rectilinear path defined by the rod and rail by the aforementioned conveyor.

As regards the size of the slides, although a nominal dimension of 3 inches×1 inch×1 mm (0.039 inches) has been mentioned, it may be appreciated that the invention may be practiced with all slides in present commercial use, ranging in size from about (3.03 to 2.92) inches×about (0.96 to 1.06) inches×about (0.0314 to 0.0485) inches. Of course for slides of significantly different sizes than those given, the positioning of the blood drop, the size of the cut-out region 68 and the applied vacuum force may vary. In achieving the desired deformation with conventional slides, a vacuum pressure of between about 15 and about 30 inches of mercury is adequate to cause a deformation of the slide effective to result in a good quality smear.

Figure 5:
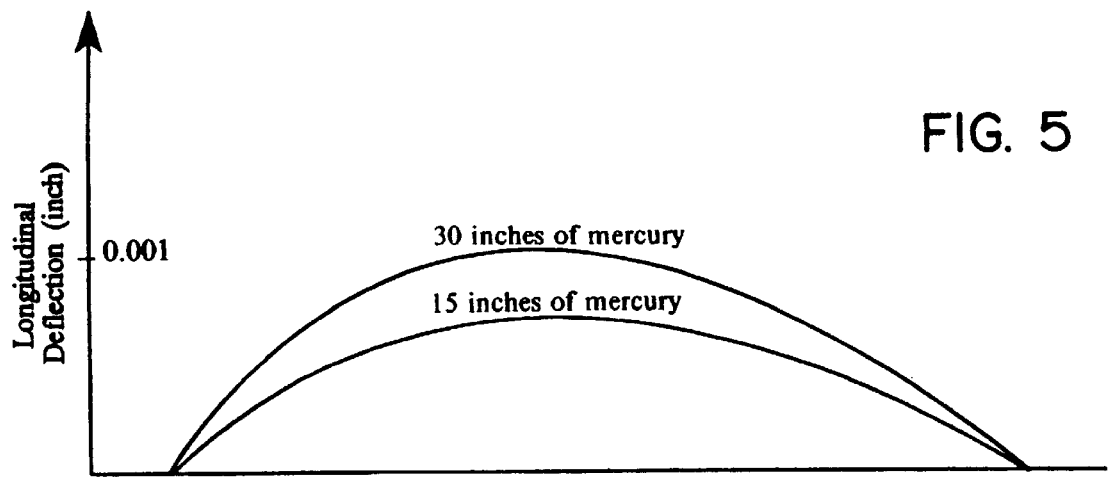
FIGS. 5 and 6 are graphs illustrating two different deformations of a portion of the slide as measured along the length and width of the slide portion, respectively.
Figure 6:
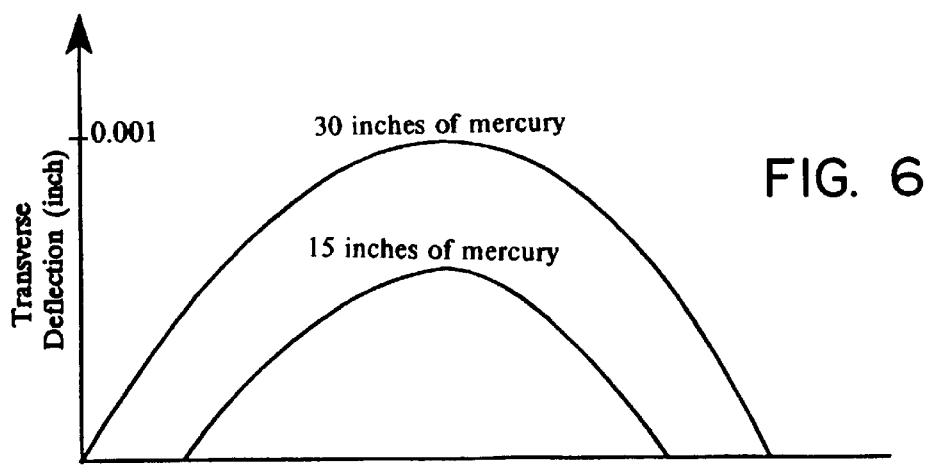

The deformation of the slide S is more clearly shown in FIGS. 5 and 6 which show in graph form the amount of deformation of the slide both from a side view as well as a cross-sectional end view as a function of two different negative pressures.

In FIGS. 7A and 7B, a blood smear slide BS as produced by the aforedescribed process is shown from the top and in cross-section. As shown in the top plan view, the slide has a label at one end which provides patient information. The smear is made from right to left, starting with a relatively large thickness, progressing down to a monolayer, and then feathering out to nothing. The monolayer region R scan examined by the clinician is the region between the dashed lines. In this region, the smear is intended to be uniformly thick, approximating a single layer of cells.

According to another aspect of the invention, movement of the blood-smearing slide S' (including its acceleration, final velocity, and the time period during which the undersurface of the smearing slide contacts the blood drop prior to being moved in the blood-smearing direction) is determined in accordance with the properties of the blood. Controlling the movement of the smearing slide is effected by controlling the rotation of the lead screw 13 and, hence, movement of the slide truck 11. The properties of the blood drop dispensed onto slide S are presumably previously determined by a hematology analyzer, for example, an analyzer commercially available under the name COULTER® STKS analyzer, made by Coulter Corporation of Miami, Fla. A blood sample is analyzed by such a device, with a portion of the blood sample being separated and stored for depositing on slide S for making a blood smear. If the making of a blood smear on a slide S for visual inspection is indicated by the analyzer, blood is then deposited on slide S for making the smear.

The results of the blood analysis from the analyzer will include seven of the parameters generated by the blood analyzer, including the hematocrit (HCT) value, hemoglobin (HGB) value, mean cell volume (MCV) value, standard deviation of red blood cell distribution (RDW) value, platelet count (PLT) value, mean platelet volume (MPV) value, and total white blood cell count (WBC) value. A significant parameter is hematocrit, which is the parameter most closely related to the viscosity of the blood. Viscosity of the blood affects the quality of the blood smear created depending on the acceleration and velocity of movement of the slide truck 11. While hematocrit is most closely related to the viscosity, it will however, be appreciated that there are blood conditions in which the hematocrit value alone will not reflect the actual viscosity. Such a situation may occur when a patient is on a medication, thus resulting in foreign substances in the blood sample, or as a result of other abnormal blood situations.

Figure 8:
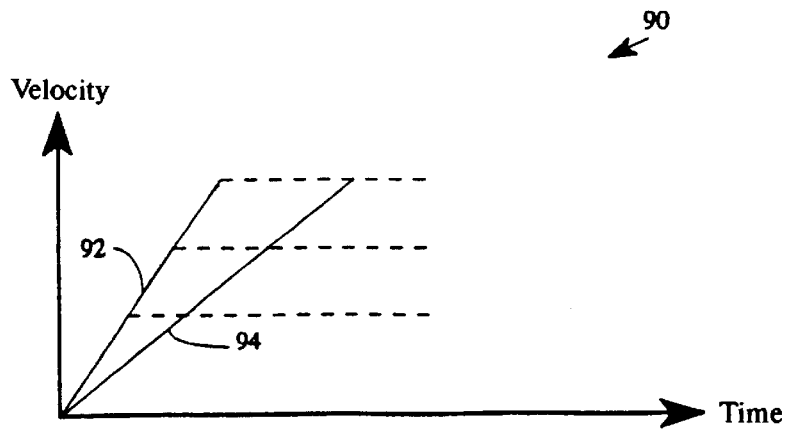
FIG. 8 is a block diagram illustrating a preferred control circuit for controlling the holding time, acceleration and velocity of the drop-smearing member used in the FIG. 1 system.
Figure 9:
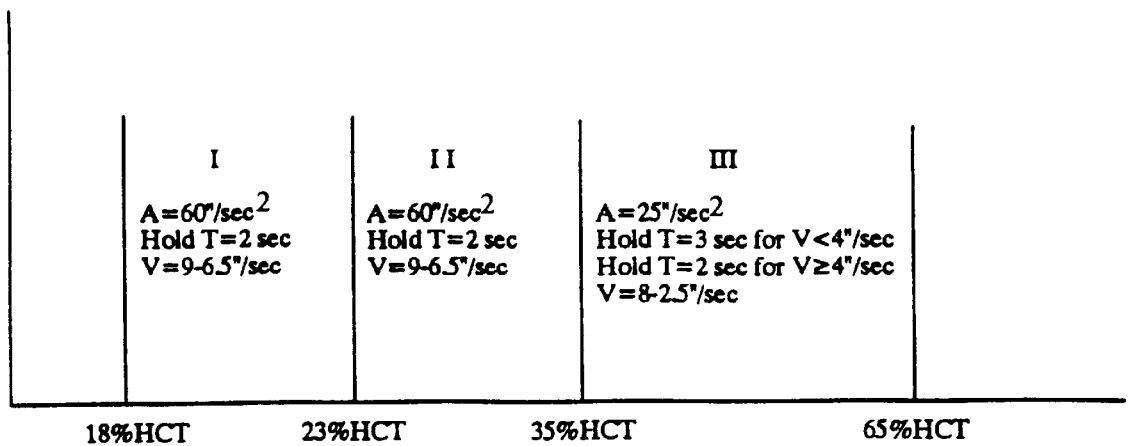
FIG. 9 is a more detailed block diagram of the control circuit of FIG. 8.

As indicated by the velocity profiles shown in FIG. 8, the invention contemplates moving the smearing slide at different accelerations and velocities to account for differences in the physical properties of the blood drop being smeared on the microscope slide. According to a preferred embodiment, the smearing slide will be moved, by appropriately rotating lead screw 13, at least two acceleration values, illustrated by curves 92 and 94 in FIG. 8, and three final velocities, shown in phantom lines. The final velocities correspond to the values shown in FIG. 9. Also, there will be at least two different "holding times" during which the smearing slide will be held motionless and in contact with the blood drop just prior to the smearing or spreading movement. For the sake of simplicity, FIG. 9 shows that using hematocrit as a base parameter, three regions can be defined with different accelerations, dwell times and final velocities. For example, Region I encompasses hematocrit values between 18% and 23%, which is typically indicative of less viscous blood. In this case, the acceleration will be set at 60 inches/sec$^2$. The holding time of the smearing slide will be about 2 seconds to enable the blood to wick along the edge of the slide by capillary action. The velocity, depending upon the equations to be employed in calculating velocity, as discussed hereafter with reference to FIG. 12, will range between 6.5 inches to 9 inches/sec.

In Region II of FIG. 9, the hematocrit values fall between 23% and 35% and such blood is typically considered to be of medium viscosity. The acceleration will also be, as in the case for Region I, 60 inches/sec$^2$. The holding time is also 2 seconds and the velocity will be between 6.5 inches and 9 inches/sec. In the more viscous blood case, as illustrated by Region III, wherein the hematocrit values fall between 35% and 65%, the acceleration is set to a value of 25 inches/sec$^2$ and the velocities are between 2.5 inches and 8 inches/sec. Two different holding times are employed, one being 3 seconds for a velocity of less than 4 inches/sec as calculated in a manner discussed hereafter with reference to FIG. 12, and the other being 2 seconds for velocities of greater than or equal to 4 inches/sec, a scenario in which although hematocrit is shown at a very high value, due to other parameters, the blood is actually less viscous than the hematocrit values would appear to suggest for reasons previously discussed.

Figure 10:
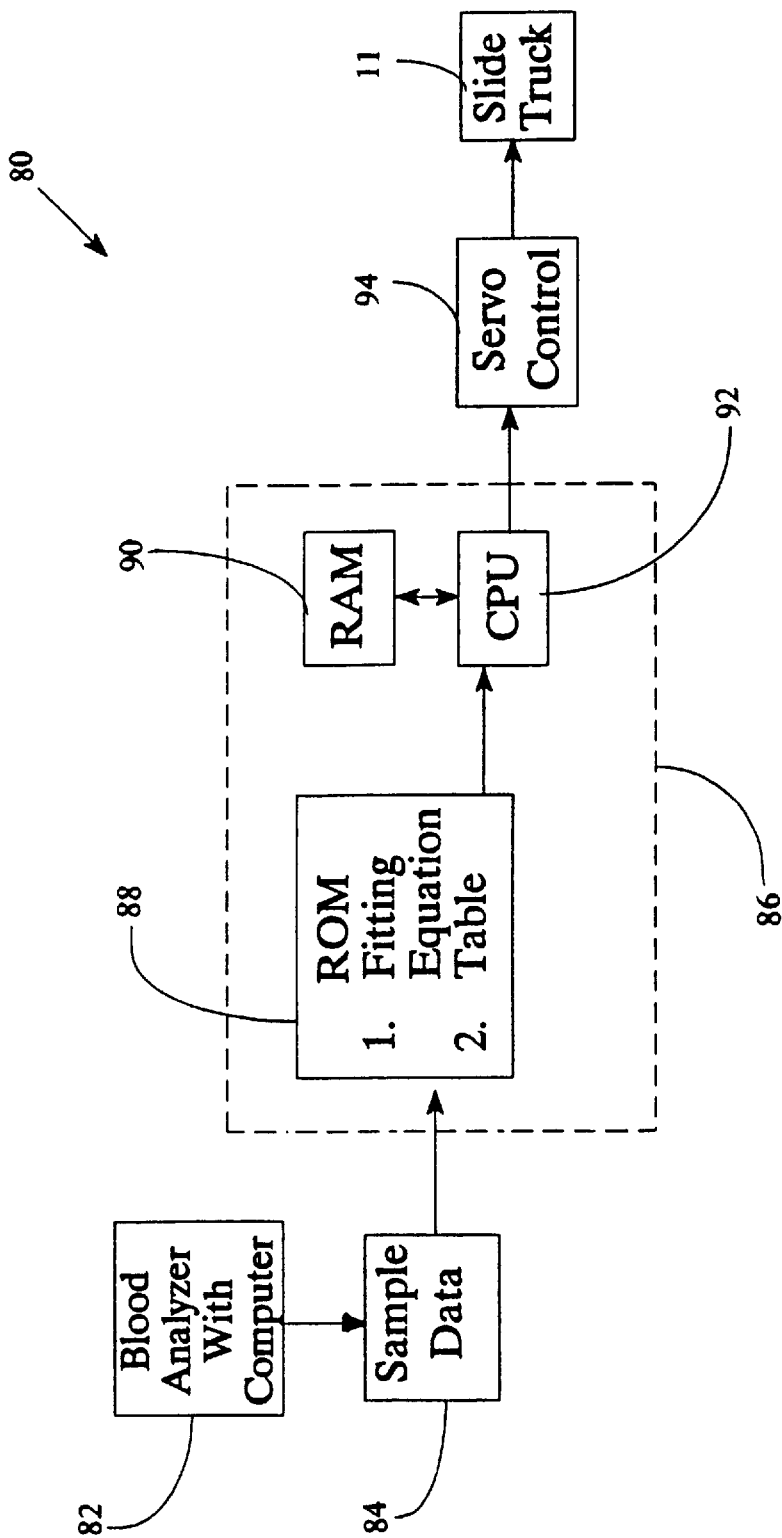
FIG. 10 is a graph illustrating two accelerations/velocity profiles in accordance with which the FIG. 8 control circuit advances the drop-smearing member.

Preferred circuitry for controlling the position of smearing slide through lead screw 13 and its stepper motor 52 is shown in FIG. 10. The circuit 80 is connected to a blood analyzer 82 which generates sample data 84 with its computer which is input through communications line into a data processing unit 86, e.g., an electronic controller board. Data processing unit 86 includes a "read only memory" (ROM) 88 which has stored therein: 1) a fitting equation, and 2) a look-up table, and generally controls the operation of the slide maker. The electronic controller board comprising the data processing unit 86 is generally conventional in nature and can be composed of a conventional central processing unit 92, such as the 80196 unit available from Intel Corporation. Either in ROM 88 or in PAL devices (not shown) the fitting equations, external conditions and other control operations can be conventionally programmed into the data processing unit 86.

The sample data 84, fitting equation and table are then loaded into RAM 90 which is operated by a central processing unit 92 to process the data from blood analyzer 82 to result in an output to a servo control 94 which controls the time of holding of the slide S' being used as a smearing blade on the drop of blood and the acceleration and velocity employed to smear the blood on slide S having the smear made thereon. The servo control 94 outputs a signal to the arrangement of the slide truck 11 with the motor to drive the motor 52 in the previously described manner.

Figure 11:
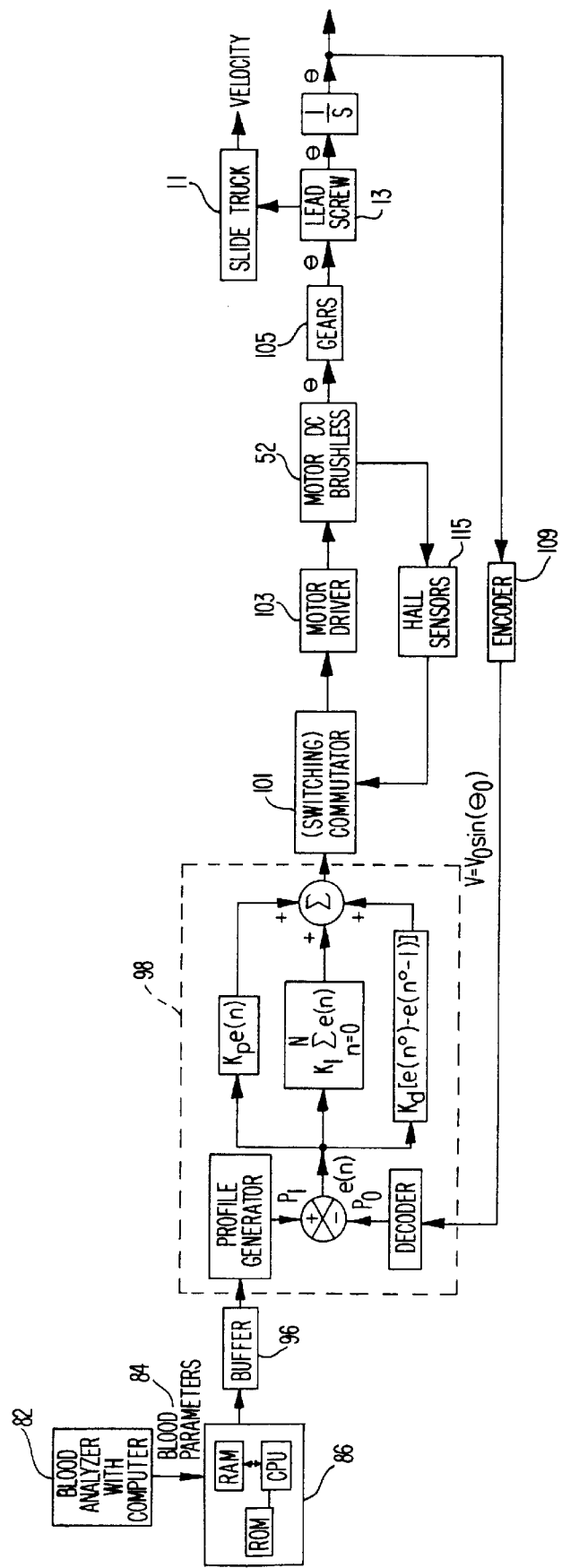
FIG. 11 is a chart illustrating in three separate regions the various acceleration, velocity and hold-time values in accordance with the preferred embodiment of the invention based on certain parameters of the drop of liquid being smeared.

FIG. 11 is a more detailed diagram showing the circuit arrangement of FIG. 8, showing the data processing unit 86, i.e., an electronic controller board, whose output goes to a buffer 96 which in turn sends its output to a controller chip 98 making up part of the servo control 94. The controller chip 98 can be, for example, the commercially available controller chip known as the LM 629 available from National Semiconductor Corporation, described in its 1990 Products Manual. This controller chip 98 implements the time of holding, acceleration and velocity profiles calculated by data processing unit 86 from the input parameters from the blood analyzer 82. The output from chip 98 is fed to a switching commutator 101, for example, one commercially available under the name LM 621, such as is available from National Semiconductor Corporation, and also described in its 1990 Products Manual. This switching commutator 101 in turn outputs a control signal to motor driver 102 which drives the stepper motor 52 of the system, i.e., a DC brushless motor, which through gears 105 connects to drive screw 13 which is operatively connected to slide truck 11.

The angular position of the shaft of the drive motor is sensed by sensors 115, for example, Hall effect sensors, to signal the switching commutator 101 to reverse current to account for the rotor of the motor 52 alternating between north and south poles of its stator.

Likewise, the position of the drive screw 13 is also transmitted to an encoder 109 back to the servo control 94 which takes the form of controller chip 98. The encoder 109 converts the sensed physical pulse representative of screw 13 position and transmits it to a decoder for conversion into a digital signal to effect digital control of the system.

Figure 12:
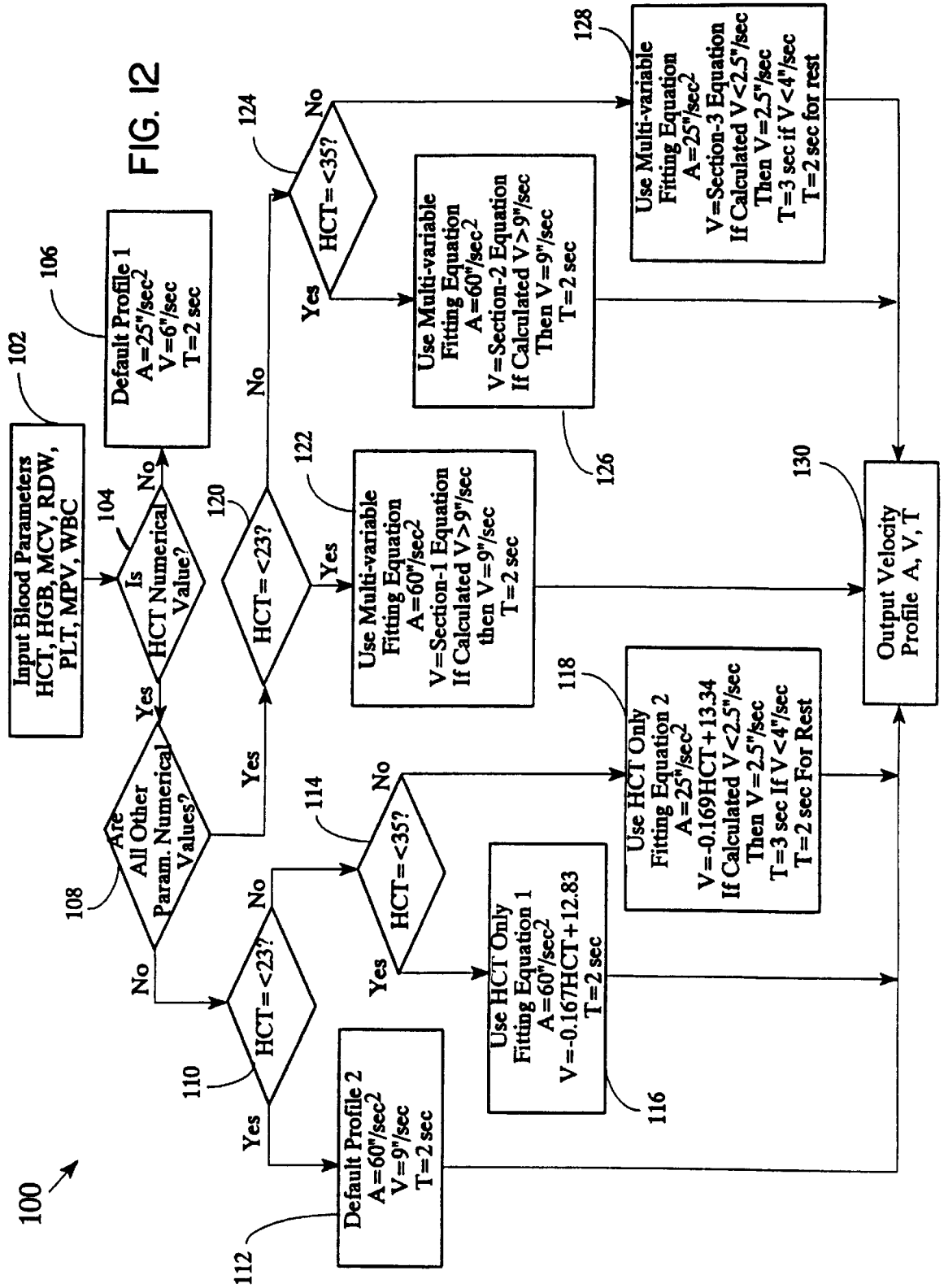
FIG. 12 is a flow chart illustrating a preferred program carried out by the control circuit for determining the hold-time acceleration and velocity of the drop-smearing member.

Implementation of the system is more clearly shown by FIG. 12 which is a flow chart illustrating how the different accelerations, velocities and holding times are calculated.

For purposes of describing FIG. 12, it is noted that the following abbreviations are defined as follows:

A=Acceleration

V=Velocity

T=Delay Time or Time of Holding on Drop of Blood

There are two default profiles where the data obtained from a hematology analyzer is not adequate, i.e., no blood parameters are obtained. Default profile number 1 results in:

A=25 inches/sec$^2$

V=6 inches/sec

T=2 sec

Default profile number 2 results in:

A=60 inches/sec$^2$

V=9 inches/sec

T=2 sec

There are situations where only a hematocrit value is obtained and at least one of the other blood parameters is not available. The equations for using only hematocrit values are:

$$V=-0.167HCT+12.83 \quad 1)$$

$$V=-0.169HCT+13.34 \quad 2)$$

In the event that all variables, i.e., are desired blood parameters are obtained, the equations employed to determine velocity are as follows:

Section I: $V=28.741+(0.060*HGB)-(0.275*HCT)-(0.114*MCV)-(0.154*RDW)-(0.007*PLT)-(0.320*MPV)+(0.253*WBC)$ Section II: $V=-1.055-(1.274*HGB)+(0.389*HCT)+(0.061*MCV)+(0.159*RDW)-(0.004*PLT)+(0.239*MPV)+(0.065*WBC)$ Section III: $V=12.587+(0.59*HGB)-(0.357*HCT)-(0.007*MCV)+(0.116*RDW)-(0.003*PLT)-(0.049*MPV)+(0.029*WBC)$ (Note: HCT is always a percentage number. Velocity is in inches per second and acceleration is in inches/sec$^2$.)

Thus, as may be appreciated from flow chart 100 of FIG. 12, there is an initial step 102 where the blood parameters from the hematology analyzer are input into the system. The blood parameters are HCT, HGB, MCV, RDW, PLT, MPV and WBC as previously defined. If the analyzer results are adequate, then numerical values for all seven parameters are given. In any case where a parameter value is not determined then an asterisk or character value is received to indicate blood analysis flags, e.g., incomplete computation. Thus, at step 104 there is an initial determination made as to whether HCT is a numerical value, i.e., has been measured. It will be appreciated that it is possible to obtain a non-numerical value from hematocrit from the hematology analyzer such as a COULTER® STKS analyzer. If HCT is not determined by the analyzer, then the first default profile is employed with an acceleration of 25 inches/sec.$^2$, a velocity of 6 inches/sec. and a hold time of 2 seconds.

If HCT is determined by the analyzer, at step 108 there is a determination made as to whether all of the other parameters have been determined. In this case it is important to appreciate that all of the other parameters must be numerical values, and if they are not numerical values then at step 110 there is a determination of whether HCT is less than or equal to a value of 23.

If HCT is less than or equal to a value of 23 then the default profile number 2 is implemented as step 112 to result in an acceleration of 60 inches/sec.$^2$, velocity of 9 inches/sec and time of holding of 2 seconds. If HCT is greater than 23, then at step 114 there is an additional determination made as to whether HCT is less than or equal to 35. If HCT is less than or equal to 35, then HCT only fitting equation number 1 is implemented at step 116 with an acceleration of 60 inches/sec.$^2$ and a hold time of 2 seconds to determine the final velocity employed. Alteratively, if HCT is greater than 35, then the HCT only fitting equation number 2 is implemented with an acceleration of 25 inches/sec.$^2$. If the calculated velocity is less than 2.5 inches/sec., then a velocity of 2.5 inches/sec. is employed. The hold time is 3 seconds if the calculated velocity is less than 4 inches/sec., and is 2 seconds for all other velocities.

In the event all other parameters are numerical values, then at step 120 an inquiry is made as to whether HCT is less than or equal to 23, and if the answer is "yes" at step 122, the multi-variable fitting equation of Section I is employed to determine velocity. Acceleration is set at 60 inches/sec.$^2$ and time of holding is at 2 seconds. If the calculated velocity results in a value of greater than 9 inches/sec the velocity is set at 9 inches/sec. If the HCT value at step 120 is greater than a value of 23, then at step 124 it is determined whether the HCT value is less than or equal to a value of 35.

In this case, at step 126 the multi-variable fitting equation of Section II is implemented with an acceleration of 60 inches/sec. and a time of holding of 2 seconds. If the resulting calculated velocity is greater than 9 inches/sec., the velocity is set at 9 inches/sec.

If the value of HCT is greater than 35 at step 124, then the multi-variable fitting equation of Section III is implemented with an acceleration of 25 inches/sec.$^2$. If the calculated velocity is less than 2.5 inches/sec., then a value of 2.5 inches/sec. is set for the velocity. The time of holding is 3 seconds if the calculated velocity is less then 4 inches/sec., and 2 seconds for the rest of the calculated values. In all cases, once the velocities are calculated, the output velocity profile is output at step 130 to be implemented by the system illustrated in FIGS. 8 and 9.

The invention has been described with reference to a particularly preferred embodiment. It will be understood, however, that modifications can be made without departing from the spirit of the invention, and such modifications are intended to be included in the accompanying claims.

What is claimed is:

1. Apparatus for making a blood smear on a microscope slide, comprising:

slide support means for supporting a microscope slide on which a blood smear is to be made;

blood supply means for depositing a drop of blood of predetermined volume on a normally planar surface of said microscope slide at a predetermined location thereon;

drop-spreading means for spreading said blood drop on a slide supported by said slide support means, thereby producing a blood smear on said slide; and slide deformation means for deforming said normally planar surface of a slide supported by said slide support means in a direction away a drop deposited thereon, said deformation being effected prior to and during the spreading of said drop by said drop spreading means, said slide deformation means comprising a vacuum source operatively connected to said slide support means for generating a vacuum pressure on said slide at a location to both hold said slide on said support means and to deform said slide.

2. The apparatus as defined by claim 1 wherein said drop spreading means comprises movably mounted means for grasping and supporting a drop-spreading member, and a rotatably driven lead screw for controlling the movement of said movably mounted means.

3. Apparatus as defined by claim 2 further comprising computing means for receiving data relating to the properties of a drop of blood to be smeared on said supported slide and for determining the speed and acceleration at which said drop-spreading member is moved to make said blood smear in a manner dependent upon the properties of the blood.

\* \* \* \* \*